United States Patent [19]

Moore

[11] 4,217,446

[45] Aug. 12, 1980

[54] ω-AMINO-2-HYDROXYALKYL DERIVATIVES OF AMINOGLYCOSIDE ANTIBIOTICS

[75] Inventor: James W. Moore, Sandwich, England

[73] Assignee: Pfizer Inc., New York, N.Y.

[21] Appl. No.: 957,873

[22] Filed: Nov. 6, 1978

Related U.S. Application Data

[63] Continuation-in-part of Ser. No. 849,875, Nov. 9, 1977, which is a continuation of Ser. No. 694,571, Jun. 10, 1976, abandoned, which is a continuation-in-part of Ser. No. 624,485, Oct. 21, 1975, abandoned.

[30] Foreign Application Priority Data

Oct. 26, 1974 [GB] United Kingdom ............... 46412/74
Oct. 24, 1975 [NZ] New Zealand ......................... 179050
Oct. 6, 1975 [ZA] South Africa ....................... 75/6326
Apr. 15, 1975 [GB] United Kingdom ............... 15425/75

[51] Int. Cl.² ..................... C07H 15/22; A61K 31/70
[52] U.S. Cl. ..................................... 536/10; 424/180; 536/17 R
[58] Field of Search ................................... 536/10, 17

[56] References Cited

U.S. PATENT DOCUMENTS

| | | | |
|---|---|---|---|
| 4,000,261 | 12/1976 | Daniels | 536/10 |
| 4,000,262 | 12/1976 | Daniels | 536/10 |
| 4,062,947 | 12/1977 | Wright et al. | 424/180 |

FOREIGN PATENT DOCUMENTS 818431 3/1975 Belgium .
835898 11/1975 Belgium .
1033394 6/1966 United Kingdom .

Primary Examiner—Johnnie R. Brown
Assistant Examiner—Blondel Hazel
Attorney, Agent, or Firm—Connolly and Hutz

[57] ABSTRACT

Certain novel 2-deoxystreptamine aminoglycoside derivatives which have an ω-amino-2-hydroxyalkyl group attached to the 1-amino group of the 2-deoxystreptamine ring, and which are useful as antibacterial agents.

10 Claims, No Drawings

ωAMINO-2-HYDROXYALKYL DERIVATIVES OF AMINOGLYCOSIDE ANTIBIOTICS

CROSS REFERENCE TO RELATED APPLICATIONS

This application is a continuation-in-part of application Ser. No. 849,875, filed Nov. 9, 1977, which is a continuation of application Ser. No. 694,571, filed June 10, 1976, now abandoned, which in turn is a continuation-in-part of application Ser. No. 624,485, filed Oct. 21, 1975, now abandoned.

BACKGROUND OF THE INVENTION

This invention relates to certain novel chemical compounds which are useful for treating bacterial infections in mammals, especially humans, and which are new members of the class of antibiotics known as aminoglycoside antibiotics. More particularly, the new compounds of this invention are derivatives of the kanamycins A and B, ribostamycin, xylostasin (the C-3″ epimer of ribostamycin), and the neomycins B and C. Said derivatives have an ω-amino-2-hydroxyalkyl residue attached to the 1-amino group of the 2-deoxystreptamine moiety, and they possess advantages in use over the corresponding aminoglycoside lacking the said ω-amino-2-hydroxyalkyl residue.

Kanamycins A and B, ribostamycin, xylostasin and neomycins B and C are well-known members of the class of antibiotics commonly known as 2-deoxystreptamine aminoglycosides (The Merck Index, An Encyclopedia of Chemicals and Drugs, Eighth Edition, 1968, P. G. Stecher, editor, Merck & Co., Inc., Rahway, N. J., pages 597, 598, 723 and 724; United States Pat. No. 3,661,892; Horii et al., *Antimicrobial Agents & Chemotherapy*, 5, 578 [1974]). Derivatives of kanamycins A and B with a 4-amino-2-hydroxybutyryl group on the 1-amino group of the 2-deoxystreptamine moiety are disclosed and claimed in U.S. Pat. No. 3,781,268, and analogous 4-amino-2-hydroxybutyryl derivatives of ribostamycin, and xylostasin (the butirosins) are described by Woo et al., *Tetrahedron Letters* 2625 (1971). Derivatives of aminoglycosides, other than the kanamycins, ribostamycin, xylostasin and the neomycins, with an ω-amino-2-hydroxyalkyl group on the 1-amino function, are disclosed in Belgian Pat. No. 818,431 (U.S. Pat. No. 4,002,742).

U.S. Pat. Nos. 3,282,783 and 3,350,387 and British Pat. No. 1,033,394 disclose a broad genus of N-alkylated derivatives of aminoglycoside antibiotics, including derivatives of the kanamycins and neomycins, in which the said N-alkyl groups can contain amino and hydroxy groups. However, these N-alkylated derivatives are reported to be substantially devoid of antibiotic properties by virtue of this alkylation.

U.S. Pat. No. 4,000,261 discloses 1-N-substituted derivatives of 5-epi-kanamycin A and 5-epikanamycin B, in which the 1-N-substituent can be aminohydroxyalkyl. U.S. Pat. No. 4,000,262 discloses 1-N-substituted derivatives of 5-epi-azido-5-deoxy-kanamycins A and B and 5-epi-amino-5-deoxy-kanamycins A and B, in which the 1-N-substituent can be aminohydroxyalkyl. U.S. Pat. No. 4,08⎵,208 discloses 1-N-substituted derivatives of 1-epi-kanamycins A and B, in which the 1-N-substituent can be aminohydroxyalkyl.

SUMMARY OF THE INVENTION

It is an object of this invention to provide novel antibacterial agents of the formula

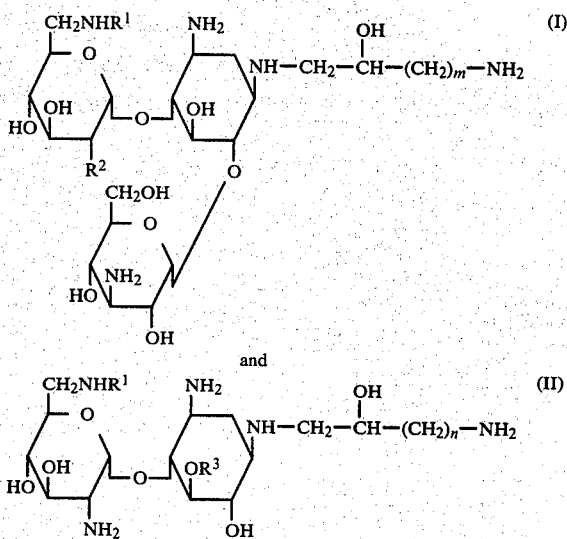

and the pharmaceutically-acceptable acid-addition salts thereof;

wherein $R^1$ is selected from the group consisting of hydrogen and alkyl having from one to four carbon atoms;

$R^2$ is selected from the group consisting of hydroxy and amino;

m is 1, 2, 3, 4, 5 or 6;

n is 1, 2, or 3;

and $R^3$ is selected from the group consisting of

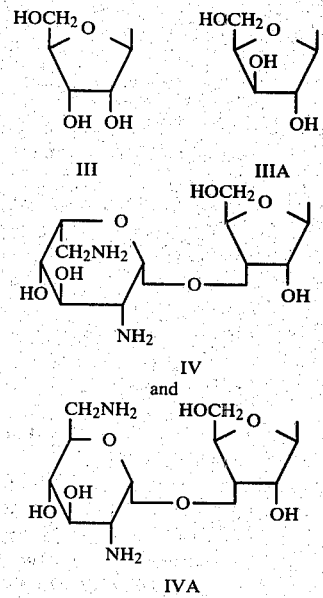

The preferred compounds of the formula I are those compounds wherein m is 1, 2, 3 or 4. A group of especially preferred compounds of the formula I consists of the compounds of the formula I, wherein $R^1$ is hydrogen, $R^2$ is hydroxy and m is 1, 2, 3 or 4. A second group of especially preferred compounds of the formula I consists of the compounds of formula I, wherein $R^1$ is hydrogen, $R^2$ is amino and m is 1, 2, 3 or 4. The preferred compounds of the invention of the formula II are the compounds of the formula II, wherein $R^1$ is hydrogen and $R^3$ is of formula III.

Particularly preferred individual compound of the invention are 1-N-[(S)-4-amino-2-hydroxybutyl]kanamycin A and 1-N-[(S)-5-amino-2-hydroxypentyl]kanamycin A.

DETAILED DESCRIPTION OF THE INVENTION

The novel compounds of the formulae I and II can be prepared according to the invention from the appropriate corresponding compound of the formula:

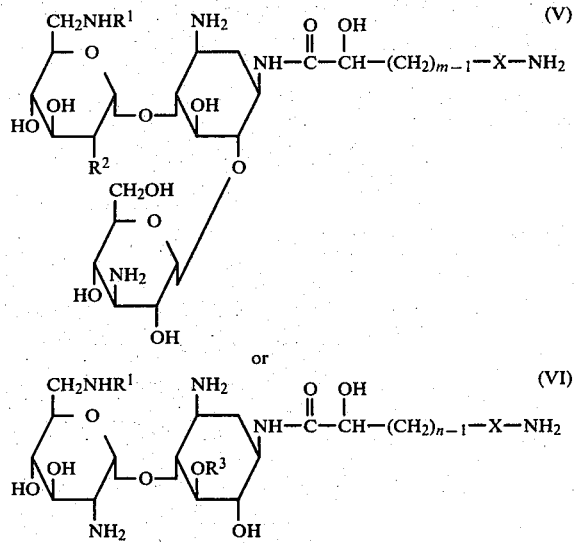

wherein $R^1$, $R^2$, $R^3$, m and n are as previously defined, and X is $CH_2$ or CO, by reaction with a reducing agent in a suitable solvent.

The aforesaid reduction of a compound of the formula V or VI involves the reduction of one or two amide groups, depending whether X is CO or $CH_2$, and a variety of agents known in the art for reducing amides can be used. For example, agents which can be used include hydride reducing agents, particularly diborane.

When reducing a compound of the formula V or VI to a compound of the formula I or II, the said compound of the formula V or VI is usually converted first to a suitable acid-addition salt, e.g. a trifluoroacetate salt, to render it soluble in organic solvents. Conversion to an acid-addition salt is carried out in conventional fashion; for example the trifluoroacetate salt can be prepared simply by dissolution in an excess of trifluoroacetic acid, at or slightly below ambient temperature, followed by removal of the excess of trifluoroacetic acid in vacuo. Reduction of a salt, e.g. the trifluoroacetate, of a compound of the formula V or VI is usually carried out by contacting the starting material with diborane in a reaction-inert, organic solvent, at a temperature in the range from about 0° C. to about 100° C., and preferably from about 25° C. to about 60° C., until the reduction is substantially complete. A reaction-inert solvent is one which does not adversely interact with either the starting reagents or the product, and typical examples of such solvents are dioxan, tetrahydrofuran and 1,2-dimethoxyethane. Although not essential, it is common to use an excess of diborane. When using an excess of diborane and working at about 50° C., the reduction reaction usually takes a few hours, e.g. from about 3 to 24 hours, to reach completion. The product is isolated in conventional fashion. For example, the excess of diborane is decomposed by the addition of water and then the organic solvent is removed by evaporation in vacuo. The residue is diluted with water, the pH is adjusted to about 5, and the product is isolated from the aqueous solution by precipitation, lyophilization or by chromatography.

The starting materials of formulae V and VI, wherein X is $CH_2$ are either known compounds, which are prepared by the published method; or they are homologues or analogues of known compounds, which are prepared by analogous methods. For example 1-N-(4-amino-2-hydroxybutyryl)kanamycin A is disclosed in U.S. Pat. No. 3,781,268. Other examples are described in U.S. Pat. Nos. 3,781,268, 3,541,078 and 3,860,574, and in published West German Patent Applications Nos. 2,350,203 and 2,322,576. The 1-N-(5-amino-2-hydroxyvaleryl) and 1-N-(3-amino-2-hydroxypropionyl) derivatives of kanamycin A and B are described in published West German Patent Application No. 2,408,666 and in J. Antibiotics, 27, 851 (1974). 6'-N-Alkyl derivatives are described in published West German Patent Application No. 2,350,169 and in J. Antibiotics, 28, 483 (1975).

Compounds of formula V and VI, where X is CO, can be derived by acylation of the 1-amino group of 2-deoxystreptamine aminoglycosides by methods analogous to those used in the preparation of compounds of formulae V and VI, where X is $CH_2$, but using as acylating agent a reactive derivative of the appropriate acid of the formula:

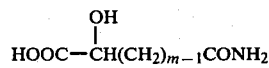

$$HOOC-\overset{\overset{OH}{|}}{CH}(CH_2)_{m-1}CONH_2$$

The acylation is carried out using standard procedures, e.g. using the N-hydroxysuccinimide ester of the 2-hydroxy-ω-carbamoylalkanoic acid.

Pharmaceutically-acceptable acid addition salts of the compounds of the invention are those formed from acids which form non-toxic acid-addition salts containing pharmaceutically-acceptable anions, such as the hydrochloride, hydrobromide, hydroiodide, sulfate or bisulfate, phosphate or acid phosphate, acetate, maleate, fumarate, oxalate, lactate, tartrate, citrate, gluconate, saccharate, p-toluene sulfonate and carbonate salts.

The compounds of this invention are derived from the naturally-occuring aminoglycoside compounds kanamycins A and B, ribostamycin, xylostasin (the C-3" epimer of ribostamycin), and neomycins B and C. The structures of these naturally-occurring aminoglycosides are known. See further: The Merck Index, An Encyclopedia of Chemicals & Drugs, Eighth Edition, 1968, P. G. Stecher editor, Merck & Co., Rahway, New Jersey, pages 597, 598, 723 and 724; Horii et al., *Antimicrobial Agents & Chemotherapy*, 5, 578 (1974). Therefore, at the points of attachment of the substituents to the various rings in the compound of formulae I and II, the stereochemistries correspond to those found in the kanamycins A and B, ribostamycin, xylostasin and neomycins B and C. These stereochemistries are as shown hereinbefore in formulae I, II, III, IIIA, IV and IVA. Included within the scope of the invention are compounds of the formulae I and II in which the ω-amino-2-hydroxyalkyl side-chain is in the (R)-configuration, compounds of the formulae I and II in which the ω-amino-2-hydroxyalkyl side-chain is in the (S)-configuration and mixtures thereof. However, when m or n is 2 or 3, the preferred configuration of the ω-amino-2-hydroxyalkyl side-chain is the (s)-configuration.

The in vitro evaluation of the compounds of the invention as antibacterial agents has been performed by determining the minimum inhibitory concentration (M.I.C.) of the test compound in a suitable medium at which growth of the particular micro-organism fails to occur. In practice, agar plates, each having incorporated therein the test compound at a particular concentration are inoculated with a standard number of cells of the test micro-organism and each plate is then incubated for 24 hours at 37° C. The plates are then observed for the presence or absence of the growth of bacteria and the appropriate M.I.C. value noted. Micro-organisms used in such tests having included strains of *Escherichia coli, Klebsiella pneumoniae, Proteus mirabilis, Pseudomonas aeruginosa, Staphylococcus aureus* and *Streptococcus faecalis*.

In vivo evaluation of the compounds have also been carried out for the more active compounds, by administering the compounds subcutaneously to mice which are exposed to a strain of *Escherichia coli*. Each compound is administered at a series of dosage levels to groups of mice and its activity is determined as the level at which it gives 50% protection, against the lethal effect of the *Escherichia coli* organism over a period of 72 hours.

For human use, the antibacterial compounds of the invention can be administered alone, or, preferably, in admixture with a pharmaceutical carrier, selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intravenously, intramuscularly or subcutaneously. For parenteral administration they are best used in the form of a sterile aqueous solution which can contain other solutes, for example, enough salts or glucose to make the solution isotonic.

For administration to human patients, the daily dosage levels of the antibacterial compounds of this invention will be comparable to those of aminoglycoside antibacterial agents currently in use, e.g. from 0.1 to 50 mg/kg (in divided doses) when administered by the parenteral routes, or from 10 to 100 mg/kg (in divided doses) when administered by the oral route. Thus tablets or capsules of the compounds will contain from 0.1 to 1 g. of active compound for administration orally up to 4 times a day, while dosage units for parenteral administration will contain from 100 to 500 mg. of active compound. The physician in any event will determine the actual dosage which will be most suitable for an individual patient, and it will vary with the age, weight and response of the particular patient. The above dosages are exemplary of the average host. There can, of course, be individual cases where higher or lower dosage ranges are merited, and such are within the scope of this invention.

The following are Examples of the preparation of novel compounds according to the invention. Temperatures are given in °C.

EXAMPLE 1

1-N-[(S)-4-Amino-2-hydroxybutyl]kanamycin A

A solution of 150 mg. of 1-N-[(S)-4-amino-2-hydroxybutyryl]kanamycin A (BB-K8; U.S. Pat. No. 3,781,268) in 10 ml. of trifluoroacetic acid was prepared at 0° C. The solution was evaporated to dryness in vacuo and dried under high vacuum at 20° C. for 15 minutes to yield a glassy solid. This was dissolved in dry tetrahydrofuran (5 ml.) and a 1 M solution of diborane in tetrahydrofuran (20 ml.) was added in portions, under an atmosphere of nitrogen. The resulting clear solution was heated at 50° C. for 3 hours, allowed to stand at room temperature for 16 hours and heated for a further three hours at 50° C. The excess diborane was decomposed by the cautious addition of a few drops of water and the organic solvent was then removed by evaporation under reduced pressure. The residue was dissolved in water (10 ml.) and basified with 0.1 N aqueous sodium hydroxide. The pH of the resulting solution was adjusted to 5 by the addition of 2 N hydrochloric acid. The solution was then chromatographed on a column containing 50 ml. of a sulfonated polystyrene, cationic ion-exchange resin, in the ammonium-ion form, eluting in turn with distilled water to remove inorganic solids, and then with a gradient of aqueous ammonium hydroxide of increasing concentration from 0.1 to 1.0 N. Fractions containing the product (as monitored by thin layer chromatography) were combined and evaporated in vacuo to give 1-N-[(S)-4-amino-2-hydroxybutyl]kanamycin A (75 mg., 50% yield), $[\alpha]_D^{25}=73°$ (c 1.0 in H$_2$O). The infrared spectrum confirmed the absence of the amide carbonyl band observed in BB-K8 at 1635 cm$^{-1}$. The mass spectrum (field desorption) showed a strong P+1 peak at m/e=572. Thin-layer electrophoresis: R$_f$=0.6 (The electrolyte was an equipart mixture of acetic and formic acids, giving a pH value of 2, and a potential difference of 900 volts was applied across the ends of the 20 cm silica coated plate for 45 minutes. Detection was performed by drying the plate, spraying with a cyclohexane solution of tertiary-butyl hypochlorite and then drying, cooling and developing the plate with starch-potassium iodide solution. Under these conditions the reference standard BB-K8 gave an R$_f$ value of 1.0 and kanamycin A an R$_f$ value of 0.9.

Analysis: Calc'd for C$_{22}$H$_{45}$N$_5$O$_{12}$.2½H$_2$CO$_3$ (percent): C, 40.5; H, 6.9; N, 9.6. Found (percent): C, 40.1; H, 6.7; N, 9.6.

A sample of the above product was converted to the volatile penta-N-acetyl-octa-O-trimethylsilyl derivative by treatment with acetic anhydride in methanol at room temperature for 24 hours, followed by reaction with a 2:1 mixture of hexamethyldisilazane and trimethylchlorosilane at room temperature for 24 hours: -M+ found 1357; C$_{56}$H$_{119}$N$_5$O$_{17}$Si$_8$ requires M+ 1357.

EXAMPLE 2

1-N-[(S)-4-Amino-2-hydroxybutyl]ribostamycin

Butirosin (1-N-[(S)-4-amino-2-hydroxybutyryl]-ribostamycin), as its free (100 mg.), was dissolved in anhydrous trifluoroacetic acid (5 ml.) at room temperature. Excess acid was removed by evaporation to dryness under vacuum to yield the trifluoroacetate salt as a glass. This was dissolved in dry diethylene glycol dimethyl ether (diglyme) (10 ml.) and a 1 M solution of diborane in tetrahydrofuran (10 ml.) was added to give a clear solution, which was allowed to stand for 18 hours at room temperature. A further 5 ml. diborane solution was added and the solution kept at room temperature for a further 24 hours. Excess diborane was decomposed by the cautious addition of a few drops of water and the organic solvents were removed under vacuum at 50° C. The residue was basified with a few drops of 2 N sodium hydroxide solution and the pH adjusted to 5 by the addition of 2 N hydrochloric acid. The product was isolated by ion-exchange chromatography as described in Example 1. Fractions containing the product in pure form were combined and evaporated under vacuum to give 1-N-[(S)-4-amino-2-hydroxybutyl]ribostamycin. Thin-layer electrophoresis: $R_f=0.5$. (The conditions were as described in Example 1; butirosin was used as the reference standard with an $R_f$ value of 1.0).

EXAMPLE 3

1-N-[(S)-5-Amino-2-hydroxypentyl]kanamycin A

1-N-[(S)-5-Amino-2-hydroxyvaleryl]kanamycin A (0.35 g.) was converted into its trifluoroacetate salt, reduced with diborane, and then chromatographed on an ion-exchange resin, according to the procedure of Example 1. This afforded 0.12 g. (35% yield) of the title compound. Thin-layer electrophoresis: $R_f=0.7$. (The conditions were as described in Example 1; the starting material was used as reference standard with an $R_f$ of 1.0).

Analysis: Calc'd for $C_{23}H_{47}N_5O_{12}.3H_2CO_3$ (percent): C, 40.4; H, 6.87; N, 9.07. Found (percent): C, 40.47; H, 6.44; N, 9.14.

EXAMPLE 4

1-N-[3-Amino-2-hydroxpropyl]kanamycin A

1-N-[3-Amino-2-hydroxypropionyl]kanamycin A was converted into its trifluoroacetate salt, reduced with diborane, and chromatographed on an ion-exchange resin, according to the procedure of Example 1. This afforded 0.04 g. (27% yield) of the title compound. Thin-layer electrophoresis: $R_f=0.6$. (The conditions were as described in Example 1; the starting material was used as reference standard with $R_f$1.0). The mass spectrum (field desorption) showed a P+1 peak at 558.

EXAMPLE 5

6'-N-Methyl-1-N-[(S)-4-amino-2-hydroxybutyl]kanamycin A

6'-N-Methyl-1-N-[(S)-4-amino-2-hydroxybutyryl]kanamycin A (J. Antibiotics, 483, 28, [1975]) was converted to its trifluoroacetate salt, reduced with diborane, and chromatographed on an ion-exchange resin, according to the procedure of Example 1, to produce 6'-N-methyl-1-N-[(S)-4-amino-2-hydroxybutyl]kanamycin A. Thin-layer electrophoresis: $R_f=0.7$. (The conditions described in Example 1 were used. The starting material had $R_f$1.0; kanamycin A and $R_f=1.03$). The mass spectrum (field desorption) showed a P+1 peak at 586.

Analysis: Calc'd for $C_{23}H_{47}N_5O_{12}.2$ 1/2H;hd 2$CO_3.6H_2O$ (percent: C, 36.08; H, 7.60; N, 8.25. Found (percent): C, 35.69; H, 6.18; N, 8.23.

EXAMPLE 6

When the procedure of Example 1 is repeated, and the starting material is:

1-N-[3-amino-2-hydroxypropionyl]kanamycin B,
1-N-[(S)-6-amino-2-hydroxyhexanoyl]kanamycin B,
1-N-[(S)-8-amino-2-hydroxyoctanoyl]kanamycin A,
1-N-[(S)-8-amino-2-hydroxyoctanoyl]kanamycin B,
6'-N-methyl-1-N-[(L)- 3-amino-2-hydroxypropionyl]kanamycin A,
6'-N-ethyl-1-N-[(S)-5-amino-2-hydroxyvaleryl]kanamycin A,
6'-N-butyl-1-N-[(S)-5-amino-2-hydroxyvaleryl]kanamycin B,
6'-N-methyl-1-N-[(S)-8-amino-2-hydroxyoctanoyl]kanamycin A,
1-N-[3-amino-2-hydroxypropionyl]ribostamycin,
6'-N-methyl-1-N-[(S)-4-amino-2-hydroxybutyryl]ribostamycin,
6'-N-propyl-1-N-[(S)-5-amino-2-hydroxyvaleryl]ribostamycin,
1-N-[3-amino-2-hydroxypropionyl]neomycin B,
1-N-[4-amino-2-hydroxybutyryl]neomycin C and
6'-N-butyl-1-N-[5-amino-2-hydroxyvaleryl]neomycin B, respectively, there is produced;
1-N-[3-amino-2-hydroxypropyl]kanamycin B,
1-N-[(S)-6-amino-2-hydroxyhexyl]kanamycin B,
1-N-[(S)-8-amino-2-hydroxyoctyl]kanamycin A,
1-N-[(S)-8-amino-2-hydroxyoctyl]kanamycin B,
6'-N-methyl-1-N-[(L)-3-amino-2-hydroxypropyl]kanamycin A,
6'-N-ethyl-1-N-[(S)-5-amino-2-hydroxypentyl]kanamycin A,
6'-N-butyl-1-N-[(S)-5-amino-2-hydroxypentyl]-kanamycin B,
6'-N-methyl-1-N-[(S)-8-amino-2-hydroxyoctyl]-kanamycin A,
1-N-[3-amino-2-hydroxypropyl]ribostamycin,
6'-N-methyl-1-N-[(S)-4-amino-2-hydroxybutyl]ribostamycin,
6'-N-propyl-1-N-[(S)-5-amino-2-hydroxypentyl]ribostamycin,
1-N-[3-amino-2-hydroxypropyl]neomycin B,
1-N-[4-amino-2-hydroxybutyl]neomycin C and
6'-N-butyl-1-N-[5-amino-2-hydroxypentyl]neomycin B, respectively.

EXAMPLE 7

1-N-[(S)-4-Amino-2-hydroxybutyl]kanamycin A

1-N-[(S)-3-Carbamoyl-2-hydroxypropionyl]kanamycin A is converted into its trifluoroacetate salt and reduced with diborane according to the procedure of Example 1, except that twice the molar amount of diborane is used. After purification using an ion-exchange column as described in Example 1, this affords the title compound.

EXAMPLE 8

Results of the testing of several of the compounds of this invention for their in vitro antibacterial activity, by the method described hereinbefore, are presented in Table I.

Table I

| Compound | MIC (mcg./ml.) | | | | |
|---|---|---|---|---|---|
| | Esch. coli | Kleb. pneu- moniae | Proteus mirabilis | Pseud. aerug- inosa | Staph. aureus |
| 1-N-[(S)-4-amino-2-hydroxybutyl]-kanamycin A | 6.2 | 3.1 | 3.1 | 1.6 | 1.6 |
| 1-N-[(S)-4-amino-2-hy- | 6.2 | 6.2 | 25 | 12.5 | 12.5 |

Table I-continued

| Compound | MIC (mcg./ml.) | | | | |
|---|---|---|---|---|---|
| | Esch. coli | Kleb. pneu- moniae | Proteus mirabilis | Pseud. aerug- inosa | Staph. aureus |
| droxybutyl]- ribostamycin | | | | | |
| 1-N-[(S)-5- amino-2-hy- droxypentyl]- kanamycin A | 6.2 | 3.1 | 12.5 | 3.1 | 1.6 |
| 1-N-[3-amino- 2-hydroxypro- pyl]kanamycin A | 12.5 | 6.2 | 12.5 | 3.1 | 3.1 |
| 1-N-[(S)-4- amino-2-hy- droxybutyl]- kanamycin B | 3.1 | 1.6 | 6.2 | 0.8 | 1.6 |
| 6'-N-methyl- 1-N-[(S)-4- amino-2-hy- droxybutyl]- kanamycin A | 6.2 | 3.1 | 6.2 | 3.1 | 3.1 |
| 1-N-[(S)-6- amino-2- hydroxyhexyl]- kanamycin A | 6.2 | 6.2 | 3.1 | 3.1 | 1.6 |

The in vivo antibacterial activity of 1-N-[(S)-4-amino-2-hydroxybutyl]kanamycin A against E. coli in mice has been measured. The compound showed a PD$_{50}$ of 3.8 mg./kg.

EXAMPLE 9

1-N-[(S)-4-Amino-2-hydroxybutyl]kanamycin B

1-N-[(S)-4-amino-2-hydroxybutyryl]kanamycin B was converted into its trifluoroacetate salt, reduced with diborane, and chromatographed on an ion-exchange resin, according to the procedure of Example 1, to give the title compound. Thin-layer electrophoresis: R$_f$=0.6 (the conditions were as described in Example 1; the starting material was used as reference standard with an R$_f$ of 1.0; and kanamycin B gave an R$_f$ value of 0.95). The mass spectrum (field desorption) showed a P+1 peak at 571.

EXAMPLE 10

1-N-[(S)-6-Amino-2-hydroxyhexyl]-kanamycin A

A solution of 1.0 g. (1.36 mmole) of 1-N-[(S)-6-amino-2-hydroxyhexanoyl]kanamycin A dicarbonate in 10 ml. of trifluoroacetic acid was prepared, and then it was evaporated to dryness in vacuo. The viscous residue was treated with 75 ml. of a 1 M solution of diborane in tetrahydrofurane, under nitrogen. The reaction mixture was then heated at 50°-55° C. for 5 hours. Evaporation of the solvent under reduced pressure yielded a gum which was dissolved in 10 ml. of 2 N hydrochloric acid. After 10 minutes the solution was basified to pH 10 with 5 N sodium hydroxide solution, and finally it was adjusted to pH 6 with 2 N hydrochloric acid. The solution was then chromatographed on a 3.5×90 cm. column containing a carboxymethyl cross-linked dextran, cationic ion-exchange resin in the ammonium form, eluting with water and a gradient of aqueous ammonium hydroxide of increasing concentration from 0 to 0.6 N. Fractions containing the product, as monitored by thin-layer chromatography, were combined and evaporated under vacuum to yield 0.64 g. (63% yield) of 1-N-[(S)-6-amino-2-hydroxyhexyl]kanamycin A. Thin-layer electrophoresis: R$_f$=0.85 (the conditions were as described in Example 1; the starting material showed R$_f$=1.0).

A sample of the above product was converted to the volatile penta-N-acetyl-octa-O-trimethylsilyl derivative by treatment with acetic anhydride in methanol at room temperature for 24 hours, followed by reaction with a 2:1 mixture of hexamethyldisilazane and trimethylchlorosilane at room temperature for 24 hours. m/e found: 1385. C$_{58}$H$_{123}$O$_{17}$N$_5$Si$_8$ requires m/e 1385.

What is claimed is:

1. A compound selected from the group consisting of

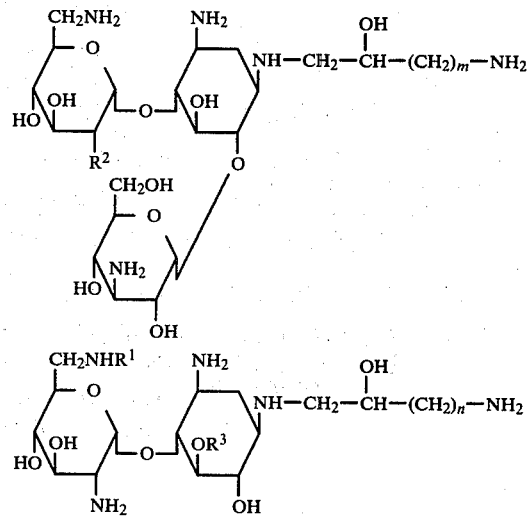

and the pharmaceutically acceptable acid-addition salts thereof;

wherein R$^1$ is selected from the group consisting of hydrogen and alkyl having from one to four carbon atoms;

R$^2$ is selected from the group consisting of hydroxy and amino;

m is 1 or 2;

n is 1, 2 or 3;

and R$^3$ is selected from the group consisting of

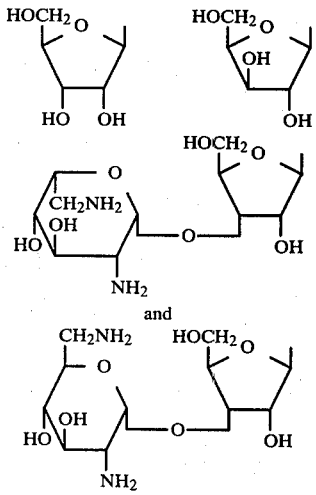

2. A compound according to claim 1 of the formula

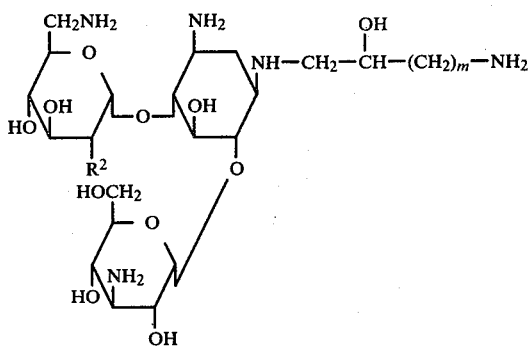

and the pharmaceutically-acceptable acid-addition salts thereof.

3. A compound according to claim 2, wherein $R^2$ is hydroxy.

4. A compound according to claim 3, wherein m is 1.

5. 1-N-[(S)-4-Amino-2-hydroxybutyl]kanamycin A, the compound according to claim 3, wherein m is 2 and the 4-amino-2-hydroxybutyl side-chain has the (S)-configuration.

6. A compound according to claim 2, wherein $R^2$ is amino.

7. 1-N-[(S)-4-Amino-2-hydroxybutyl]kanamycin B, the compound according to claim 6, wherein m is 2 and the 4-amino-2-hydroxybutyl side-chain has the (S)-configuration.

8. A compound according to claim 1 of the formula:

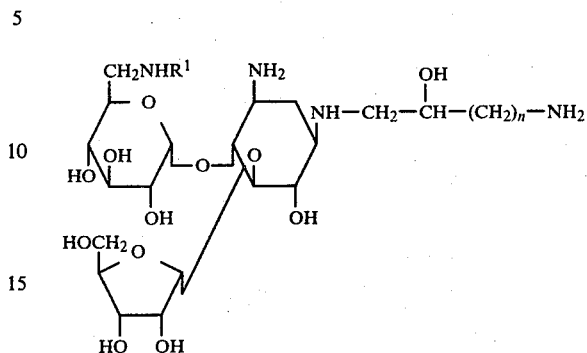

and the pharmaceuticall-acceptable acid-addition salts thereof.

9. A compound according to claim 8, wherein $R^1$ is hydrogen.

10. 1-N-[(S)-4-Amino-2-hydroxybutyl]ribostamycin, the compound according to claim 9, wherein n is 2 and the 4-amino-2-hydroxybutyl side-chain has the (S)-configuration.

* * * * *